(12) United States Patent
Jutila et al.

(10) Patent No.: US 10,149,784 B2
(45) Date of Patent: Dec. 11, 2018

(54) INSERTER FOR AN INTRAUTERINE SYSTEM

(75) Inventors: Ilkka Jutila, Sauvo (FI); Heikki Lyytikäinen, Naantali (FI)

(73) Assignee: Bayer Oy, Turku (FI)

( * ) Notice: Subject to any disclaimer, the term of this patent is extended or adjusted under 35 U.S.C. 154(b) by 848 days.

(21) Appl. No.: 13/882,264

(22) PCT Filed: Oct. 26, 2011

(86) PCT No.: PCT/FI2011/050933
§ 371 (c)(1),
(2), (4) Date: Jun. 11, 2013

(87) PCT Pub. No.: WO2012/056105
PCT Pub. Date: May 3, 2012

(65) Prior Publication Data
US 2013/0255695 A1 Oct. 3, 2013

(30) Foreign Application Priority Data
Oct. 29, 2010 (FI) ..................... 20106131

(51) Int. Cl.
*A61F 6/18* (2006.01)
*A61F 6/14* (2006.01)

(52) U.S. Cl.
CPC ............... *A61F 6/18* (2013.01); *A61F 6/144* (2013.01)

(58) Field of Classification Search
CPC ...... A61F 6/00; A61F 6/06; A61F 6/12; A61F 6/14; A61F 6/142; A61F 6/144;
(Continued)

(56) References Cited

U.S. PATENT DOCUMENTS

| 5,785,053 A | 7/1998 | MacAndrew et al. |
| 6,056,976 A | 5/2000 | Markkula et al. |

(Continued)

FOREIGN PATENT DOCUMENTS

| CN | 1168626 | 12/1997 |
| CN | 1377635 | 11/2002 |

(Continued)

OTHER PUBLICATIONS

International Preliminary Report on Patentability for International Patent Application No. PCT/FI2011/050933, dated Apr. 30, 2013, 4 pages.

(Continued)

*Primary Examiner* — Kari Rodriquez
*Assistant Examiner* — Camtu Nguyen
(74) *Attorney, Agent, or Firm* — IP Spring

(57) ABSTRACT

An inserter for an intrauterine system includes a handle. The handle has a longitudinal opening at its first end, the opening having a longitudinal axis parallel to the longitudinal axis of the inserter, a first end and a second end, a movable slider arranged in the longitudinal opening and having a first end and a second end. The inserter also includes a movable plunger and an insertion tube arranged around the plunger having a first end and a second end, with its second end attached to the slider. The handle further includes a lock for reversibly locking the intrauterine system in relation to the plunger via a removal string of the intrauterine system, the lock being attached to the plunger and being controllable at least by a part or an extension of the slider and/or of the insertion tube or of the handle.

10 Claims, 8 Drawing Sheets

(58) Field of Classification Search
CPC .. A61F 6/18; A61F 2/2436; A61F 2/95; A61F 2/962; A61F 2/966; A61F 2/97; A61F 6/146; A61F 2002/9505; A61F 2002/9528; A61F 9/00781; A61K 9/0039; A61K 9/02; A61K 9/20; A61K 9/50; A61B 17/4241; A61M 2039/0279
USPC .................................................. 128/839–841
See application file for complete search history.

(56) References Cited

U.S. PATENT DOCUMENTS

| | | | |
|---|---|---|---|
| 6,299,027 | B1 | 10/2001 | Berge et al. |
| 2003/0028236 | A1* | 2/2003 | Gillick ............... A61F 2/95 623/1.11 |
| 2004/0163650 | A1* | 8/2004 | Lowe ................. A61F 6/18 128/830 |
| 2007/0123904 | A1 | 5/2007 | Stad et al. |
| 2009/0069890 | A1* | 3/2009 | Suri ................ A61F 2/2436 623/2.11 |
| 2009/0105794 | A1* | 4/2009 | Ziarno ............. A61F 2/2436 607/120 |
| 2010/0049313 | A1* | 2/2010 | Alon ................. A61F 2/2418 623/2.11 |
| 2010/0168756 | A1* | 7/2010 | Dorn ................ A61F 2/95 606/108 |
| 2011/0079226 | A1* | 4/2011 | Sakhel .............. A61B 1/303 128/830 |
| 2011/0238147 | A1* | 9/2011 | Bennett ............. A61M 25/01 623/1.11 |

FOREIGN PATENT DOCUMENTS

| | | |
|---|---|---|
| CN | 201104943 | 8/2008 |
| CN | 101360523 | 2/2009 |
| CN | 201505207 | 6/2010 |
| DE | 29819558 | 2/1999 |
| EP | 0798999 | 10/1997 |
| EP | 1691740 | 8/2006 |
| WO | 00/00550 | 1/2000 |
| WO | 2003/017971 | 3/2003 |
| WO | 2010/031899 | 3/2010 |
| WO | 2010/031900 | 3/2010 |
| WO | 2010/031902 | 3/2010 |

OTHER PUBLICATIONS

International Search Report and Written Opinion for International Patent Application No. PCT/FI2011/050933, dated Mar. 5, 2012, 7 pages.

* cited by examiner

INSERTER FOR AN INTRAUTERINE SYSTEM

FIELD OF THE INVENTION

The present invention relates to an inserter for an intrauterine system, comprising a handle having a longitudinal opening at its first end, said opening having a longitudinal axis parallel to the longitudinal axis of the inserter, a first end and a second end, a movable slider arranged in said longitudinal opening and having a first end and a second end, a movable plunger, an insertion tube arranged around the plunger having a first end and a second end, with its second end attached to the slider, locking means for reversibly locking the intrauterine system in relation to the plunger via a removal string of the intrauterine system, said locking means being attached to the plunger and being controllable at least by a part or an extension of the slider and/or of the insertion tube or of the handle. The invention also relates to a kit comprising an inserter.

BACKGROUND OF THE INVENTION

Various types of inserters have been developed for the positioning of mechanical and copper wire-containing intrauterine devices (IUDs) as well as of intrauterine systems having a drug containing cylinder (IUSs). In the following, IUD and IUS can be used interchangeably and when one is mentioned, it is to be understood that either of them can be used.

Simple rod-shaped inserters have been suggested for inserting relatively small or sufficiently flexible intrauterine devices in their original, expanded shape by using simple push-in technique. However, common inserters are mostly constructed for introducing the device into the uterus in a contracted state to minimize the pain during insertion. These inserters usually comprise an insertion tube having a relatively narrow diameter and a rounded, blunt end which will pass through the cervical canal easily and will not damage or injure the fundus upon contact therewith, and a plunger inside the insertion tube. Prior to insertion the device, whether an IUD or an IUS is usually retracted into the insertion tube either by drawing the string(s) attached to the device and intended for the removal of the device from the uterus, or by keeping the strings steady and pushing the insertion tube towards the device. Then the insertion tube with the device therein is introduced through the cervical canal into the uterus. When the device is correctly positioned, it is released either by pushing the plunger towards the uterus or commonly by holding the plunger steady and by retracting the insertion tube backwards, to the direction opposite to the uterus. Once released from the insertion tube within the uterine cavity, the device is supposed to resume its original expanded shape A typical example of an intrauterine device has a T-shaped body fabricated of plastic material and consisting of an elongated body part having at one end a transverse member comprising two wings, the elongate member and the transverse member forming a substantially T-shaped piece when the device is in the expanded configuration, for example positioned in the uterus. The tips of these wings are preferably hemispherical in order to facilitate the introduction of the device through the cervical canal. The elongate member has a copper spiral or wire or a drug containing capsule arranged on the body. The end of the vertical body part has a loop with a string or strings attached to it, with which the device can be removed from the uterus after use or whenever needed.

The diameter of the elongate member in intrauterine systems having a drug containing cylinder is greater than in copper wire-containing IUDs or mechanical devices, and thus the diameter of the insertion tube also has to be larger. However, since the frames of these intrauterine systems, or in the commonly used T-shaped systems the hemispherical ends of the transverse member, are small in relation to the diameter of the insertion tube, the correct positioning of the IUS within the insertion tube will be extremely important. Therefore proper handling of the removal string(s) is absolutely needed during the preparatory steps and during insertion, as well as when finally releasing the IUS after insertion. Challenging steps, which will be exemplified with a common T-shaped device, apply as well to intrauterine systems having another type of frame, for example 7-shaped or closed, continuous frames For the insertion of a T-shaped intrauterine system it is extremely important that the hemispherical ends of the transverse member are in the exactly correct position in relation to the edge of the insertion tube at the moment of introducing the device in the uterus. If the IUS is pulled into the insertion tube by means of the removal string, which is usually the case with the existing devices, it is understandable that it is difficult to make the IUS stop in the correct position, especially if the relative movement of the insertion tube with respect to the plunger is not restricted by any stop member. Pulling with too much force easily makes these ends enter almost completely into the insertion tube. During the insertion of the device, the sharp edges of the insertion tube may interfere with the introduction of the device through the cervical canal. On the other hand, if the device is not drawn deep enough into the insertion tube, the frame ends remaining outside the insertion tube project outwardly. The diameter at the level of the wings remains too wide, which makes the introduction of the device more difficult. It is easier to make the wings stop in the correct position in the case of copper-wire devices, because then the insertion tube is relatively narrow in relation to the wings and therefore there is no risk of the wings being drawn too deep into the tube even by forceful pulling.

It is also important that the device is pulled into the insertion tube in a correct direction, i.e. parallel to the axis of the insertion tube, so that the loop, the rest of the body or the string(s) will not be damaged. If the device is pulled in the insertion tube or onto the plunger in a wrong angle or position, the edges of the insertion tube easily damage the loop or the body of the IUS. In the worst case the device will be stuck in the insertion tube. If pulling is continued and the device does not turn into the correct position, the string(s) will finally cut through the loop or the body, after which the device and the inserter cannot be used anymore. Further, after the device has been inserted in the uterus the strings have to be released at a right moment so that withdrawing of the inserter will not expel the IUS or move it from the correct position.

The European patent EP 1 691 740 relates to an inserter, with which the correct positioning and directional stiffness of the device in the inserter prior to and during insertion can be ensured, for instance, by shaping the forward end of the plunger such that the IUS assumes a specified constant configuration when drawn into the insertion tube. The IUS will thus not be twisted during insertion.

European patent EP 798 999 relates to an inserter, which allows the correct positioning of an IUS also in those cases in which the elongate member of a T-shaped device contains active material, which involves a diameter larger than that of an elongate member of a copper-wire IUD. The inserter comprises a plunger, a handle attached to the plunger, a string for the removal of the IUS, a cleft on the end of the handle to lock the string(s) in such a way that the IUS remains immobile in relation to the plunger, and an insertion tube around the plunger. The IUS is drawn into the insertion tube by pushing the tube over the device or by pulling on the removal threads where after the threads are manually locked in the cleft. The relative movement of the plunger and the protective tube is restricted by a stop member or stop members to ascertain that the correct configuration of the IUS is achieved. The stop members ensure that the front edge of the insertion tube is stopped in a configuration in which the hemispherical tips of the T-wings remain partly uncovered by the insertion tube but the wings nevertheless remain pressed against each other. This inserter overcomes many of the problems encountered with the conventional inserters, but the stop members have to be managed and the string(s) still need to be manually handled and locked.

International patent application WO 2010/031900 relates to an inserter comprising a movable slider arranged in a longitudinal opening of the handle, a solid plunger attached to the handle, an insertion tube arranged around the plunger with its second end attached to the slider and means for reversibly locking the intrauterine system in relation to the plunger via a removal string of the intrauterine system. The locking means is attached to the handle and is controllable by the slider and/or the insertion tube.

OBJECT AND SUMMARY OF THE INVENTION

An object of the invention is to provide a simple, easy to use inserter for the positioning of an intrauterine system in the uterus and a kit comprising an intrauterine system and said inserter. An object of the invention is particularly to provide an inserter and a kit with which, during the insertion process, no manual handling of the strings or the IUS is needed. An object of the invention is especially to provide an inserter wherein the relative movement of the insertion tube can be shorter as compared to previous inserters, as this would lead to a more accurate insertion and minimise the possibility of the IUS to be stuck in the insertion tube.

A further object of the invention is to provide an inserter comprising a locking means for reversibly locking the intrauterine system in relation to the plunger via removal string(s) of the intrauterine system, said locking means being attached to the movable plunger.

A typical inserter for an intrauterine system according to the present invention, comprises
  a handle having a longitudinal opening at its first end, said opening having a longitudinal axis parallel to the longitudinal axis of the inserter, a first end and a second end,
  a movable slider arranged in said longitudinal opening and having a first end and a second end,
  a movable plunger,
  an insertion tube arranged around the plunger having a first end and a second end, with its second end attached to the slider,
  locking means for reversibly locking the intrauterine system in relation to the plunger via a removal string of the intrauterine system, said locking means being attached to the plunger and being controllable by at least a part or an extension of the slider and/or of the insertion tube or of the handle.

A typical inserter according to this invention further comprises movement means (18), which comprise a rotation part (19) arranged to rotate around a rotation axis that is perpendicular to the longitudinal axis of the inserter, the rotation part (19) being arranged in functional connection with the plunger (2) and with the slider (5), such that the movement of the slider (5) generates simultaneous movement of the plunger (2) and of the insertion tube (6) along the longitudinal axis of the inserter, in opposite directions.

The present invention also relates to a kit comprising an intrauterine system and an inserter according to the present invention.

DETAILED DESCRIPTION OF THE INVENTION

The inserter according to this invention thus comprises at least one element interconnected on at least one point to a means or member which can pivot, turn or rotate with respect to the longitudinal axis of the handle and the inserter in a way that the movement of the slider thus generates the movement of the insertion tube and the plunger at the same time but to opposite directions, via pivoting, turning or rotation of the rotation part. The movement of the slider also causes the release of the removal string or strings of the intrauterine system as soon the IUS has correctly been positioned in the uterus. Thus, with the present invention, no manual handling of the strings as such is needed, which increases accuracy and hygiene of the insertion procedure. A person skilled in the art is readily able to design such devices and some examples are given in connection with the drawing.

The rotation axis of the rotation part is perpendicular to the longitudinal axis of the inserter, but also preferably perpendicular to a plane comprising the longitudinal axis of the inserter and defining the main plane of the inserter. The rotation axis can also be for example perpendicular to the side wall of the inserter, and thus comprised in the above-mentioned plane.

The most preferred kit comprising an inserter and an intrauterine system, according to the present invention, is such that
  the inserter is according to the present invention,
  the intrauterine system comprises a therapeutic component and a frame, the therapeutic component being connected to the frame at at least one point, and
  in the original, starting position the lower part of the frame and/or the therapeutic component is at least partly arranged inside the first end of the insertion tube and the rest of the frame and/or the therapeutic component is mainly arranged outside the first end of the insertion tube In the following, several different embodiments of the present invention, both the inserter and the kit, are discussed. The information given applies mutatis mutandis to both the inserter and the kit. The invention therefore provides an easy to use inserter and kit comprising the device and the inserter, by which only few simple steps are needed to prepare for the insertion and to securely install, position and release an intrauterine system into the uterus so that no manual handling of the removal string(s) or the IUS itself will be needed.

In the present description and claims, by first ends are typically meant the ends that are closer to the uterus during the insertion of the intrauterine system. Second ends are the ends opposite to the first ends. Moreover, the terms IUS or IUD are used when describing the preferred embodiment of the present invention, but these are not to be construed as limiting the claims. The term removal string means one or more strings attached to the IUS and used for removing the system once it reaches the end of its use time. There may thus be one or more such strings, and this term encompasses also strings that are not used for removal but only for locking the device during insertion.

According to an embodiment of the invention, the slider comprises a longitudinal part, the movement means comprises a longitudinal movement part that is essentially parallel to the longitudinal part and the longitudinal part and the movement part are arranged in a functional connection with the rotation part.

According to another embodiment, at least one of the longitudinal part and the movement part is in the form of a tooth rack, and the rotation part is in the form of a cogwheel.

The inserter according to the invention is suitable for the positioning of intrauterine devices and intrauterine systems having different sizes and shapes as long as these can be managed to enter the insertion tube by appropriate arrangements.

Thus the frame can for example have a shape of T, 7 or S, or the shape is selected from the group consisting of annular, circular, oval, spiral, toroidal, triangular, polygonal, almond-shape, shield-shape and diamond-shape. The frame is preferably made of an elastic material, such as an elastomer composition. The frame may include, for example as a core material, a thin fibre or wire made of suitable polymer or metal, for example of a shape memory material or other suitable material that is elastic enough for allowing the insertion, i.e. collapsing during the insertion through the cervical canal but returning to its original shape once in place in the uterus.

The therapeutic component is a component capable of inducing a therapeutic effect, for example by releasing an active agent such as copper ions or hormones According to an embodiment of the invention the therapeutic component is selected from the group consisting of a reservoir for an active agent, a metallic wire or a sleeve and a combination thereof. For example, the reservoir may essentially consist of an elastomer comprising therapeutically active agent(s), or the metal wire or sleeve can be made of copper.

According to another embodiment of the invention, the reservoir of the intrauterine system essentially consists of an elastomer comprising therapeutically active agent(s). The reservoir is known in the art and can be for example as described in WO 2003/017971, U.S. Pat. Nos. 6,056,976, 6,299,027 or WO 00/00550, the contents of which are hereby incorporated by reference.

The elastomer can be for example an elastomer composition comprising a siloxane based elastomer, a thermoplastic polyurethane, a thermoplastic polyurethane elastomer, ethyl vinyl acetate copolymer, a polyolefin-based elastomer, a silicone containing thermoplastic polyurethane or a mixture of at least two of these. The reservoir may also be of a core and membrane-type, wherein both parts are preferably made of an elastomer composition, either the same or different.

According to a further embodiment of the invention, the therapeutic component is connected to the frame at at least one point.

The intrauterine system comprises strings for removal, location or detection of the system. It may also comprise at least one image enhancing means for improving the detection and/or location of the system. The image enhancing means can be for example selected from the group consisting of an inert metal coating on at least part of the body of the intrauterine system, inert metal inserts, clips, rings or sleeves fixedly positioned on the body of the intrauterine system, metal or ferromagnetic powder or particles or suitable metal or alkali metal salts mixed during the compounding step in the raw materials of the frame, core matrix or membrane of the intrauterine system, and a metallic cup, connector, adapter, clamp, sleeve or holder fixed at a suitable position on the frame, which can also be used to anchor or join the therapeutic component onto the frame.

According to an embodiment of the invention, the first end of the opening and the first end of the slider form a first pair of stop members, and the second end of the opening and the second end of the slider form a second pair of stop members. The first pair of stop members thus indicates the moment when the intrauterine system is retracted in the insertion tube and the second pair of stop members indicates the moment when the intrauterine system is outside the insertion tube and the strings are released.

The handle of the inserter can have many shapes and is designed for easy handling of the inserter by using only one hand. A part of the handle comprises an opening having a first end and a second end and running in the longitudinal direction of the plunger. The handle also has at its first end a channel in which the insertion tube and the plunger can slide in the longitudinal direction. At the second end, i.e. distal end (away from the uterus) the insertion tube is attached to the slider or to a means which can be used to move the slider and preferably forms at least a part of the slider. With respect to the starting configuration, the front surface of said means and the surface at the first end of the opening (the end directed towards the IUS) together form the first pair of stop members. By simply pushing the slider or the means for moving the slider forwards in the opening the slider arrangement and the insertion tube attached to it will move toward the first end of the opening and at the same time the plunger will move back toward the second end of the opening. The distance the insertion tube and the plunger apart corresponds substantially to the length of the IUS assembled for insertion (which for example for a T-shaped device is larger than the length when the system is at its "free" position and corresponds approximately to the length of the longitudinal part plus the length of the wing). This can also be called the compressed state of the IUS. Because the string(s) and the IUS remain immobile all the time, the IUS is retracted in the insertion tube. When the IUS has been positioned in the uterus the slider will be pulled backwards, which causes the insertion tube to move back towards the second end of the handle and the plunger to move forward towards the uterus. The slider is pulled until the second pair of stop members abut, and at this stage the removal strings will be unlocked and the IUS released.

The longitudinal opening on the handle can be quite narrow and does not need to be symmetrically positioned on the handle and with respect to the longitudinal axis.

The plunger is advantageously hollow or has a groove or bore running in the axial direction thus allowing the string(s) to locate and slide freely in it, without any risk of them getting jammed between the plunger and the insertion tube. The first end, i.e. the forward end of the plunger is preferably suitably shaped to have for example a notch, an indentation, an eyelet, a funnel or a groove to adapt to the lower end of the intrauterine system and to enable the optimal and secure positioning of the intrauterine system on the plunger According to an embodiment of the invention the first end of the insertion tube comprises at least one frame slot for receiving the frame of the intrauterine system. The frame slots are preferably parallel to the longitudinal axis of the insertion tube but may also be non-parallel to it. The frame slots are preferably narrow enough to keep the IUS on place and designed to facilitate the stretching /compression of the frame during the first insertion step, when the IUS is pulled into the insertion tube.

The forward parts (parts directed towards the uterus) of the plunger and the insertion tube can be straight or curved so as to conform to the anatomy of the uterus. Preferably these parts are made from a sufficiently flexible material in order to avoid perforation of the uterus.

The slider mechanism is preferably inside the handle and comprises at least one element, for example an elongated element, which can be moved in the longitudinal direction of the plunger. According to an embodiment of the invention the slider comprises means to move the slider, which preferably is a part of the slider, and the insertion tube attached to the slider or to said means. According to another embodiment of the invention the slider comprises at least two elements, preferably parallel, which are interconnected on at least one point by a means or member capable of pivoting or turning with respect to the longitudinal axis of the handle and thus capable of generating the simultaneous movement of the insertion tube and the plunger. The at least one element and the interconnecting means or member comprise for example a tooth rack and a cogwheel.

The handle preferably comprises one or more means to guide or connect the slider elements and to facilitate the correct movement of the slider and/or the plunger, for example a support, a shoulder, a holder, a saddle, a groove or a slot. The slider, the means to move the slider or the insertion tube or the handle preferably comprises at least one structural element, for example an extension, which is capable to generate the necessary operation of the locking means to release the pre-locked string(s) when the slider is in the backward position, i.e. when the second pair of stop members abut.

The locking means is any arrangement which immobilises the removal string(s) to hold the IUS in a stable position with respect to the plunger and, which induced by the movement of the slider or of the means to move the slider or the insertion tube or the plunger itself automatically releases the string(s) after insertion to release the IUS. Particularly, the invention relates to a locking means which comprises an object capable of reversibly preventing and/or allowing the movement of the string(s) by at least partly moving or pivoting from the original position, for example rotating around a shaft or an axle, and vertically or horizontally attached to the plunger. The object may have several shapes and may be for example round or rod-shaped, wedge, polygonal or rectangular with rounded or sharp corners. The surface of the object preferably comprises one or more extensions having variable size and shape, for example a knob, a rib or a switch When the slider mechanism or the insertion tube is moving backwards or the plunger is moving forwards, at a suitable point a part or an extension of the handle, the slider or of the insertion tube is pressed against at least one extension of the object thus changing its orientation enough relative to the original position to cause release of the string(s). Preferably the object has a slot or a pinhole through which the string(s) run. The locking means may also comprise at least one counterpart against which the string(s) are pressed by the object and thus reversibly immobilized in the locking position. The counterpart has a suitable shape adapted to fit at least some part of the surface of the object. An extension, or extensions of the object can be used to keep the object and the counterpart in a fixed configuration until the IUS should be released. The counterpart preferably has a suitable design to keep the string(s) in proper direction, for example a slot or pinhole through which the string(s) run. Further, the object and said at least one counterpart have preferably a suitable length and diameter to fit inside the handle According to one embodiment of the invention, the locking means thus comprises
 a main part,
 a first extension of the main part having an abutment surface,
 a counterpart adapted to form a blocking together with the main part,
wherein the locking means is rotatably mounted on the plunger.

The locking means can be rotatably mounted on the plunger for example via the main part.

According to another embodiment of the invention the main part comprises an opening or a slot in a diagonal direction through essentially the whole diameter of the main part, adapted to receive at least one removal string of the intrauterine system.

According to yet another embodiment of the invention, the locking means comprises
 a main part,
 a first extension of the main part having an abutment surface,
 a second extension of the main part having a wedge-like shape,
 a counterpart
wherein the second extension is adapted to form a blocking together with the counterpart and the locking means is rotatably mounted on the plunger The locking means is thus mounted on the plunger of the inserter. According to one embodiment of the invention, the main part has essentially the shape of a cylinder, or it is of triangular shape, or of any other suitable shape.

According to one embodiment of the invention the slider comprises an extension adapted to abut on the abutment surface of the first extension of the main part of the locking means According to one other embodiment of the invention the locking means comprises a main part comprising a first extension and a second extension arranged, in their initial position, to be essentially in contact with each other to from a blocking, and wherein the slider, a part of the slider, the insertion tube or a part of the insertion tube is arranged to protrude into the main part of the locking means so as to separate the first and second extensions from each other.

According to yet one other embodiment of the invention the locking means comprises
 a first locking part and a second locking part movably mounted on the plunger and arranged, in their initial position, to be essentially in contact with each other to form a blocking, and
 a first protrusion and a second protrusion arranged on a location selected from the group consisting of the inner surface of the insertion tube, the outer surface of the insertion tube, the inner surface of the slider and the outer surface of the slider,
wherein the first and second protrusions are arranged so as to move the first and second locking parts to a second position when moving the insertion tube.

The locking means could also be welding, gluing, cutting, knot or adhesion. The strings could thus be for example attached to the body of the plunger by welding (for example by heating), gluing with glue or attaching with an adhesive agent (such as sticker). The slider for example would then release the attachment at a correct stage when the IUS is to be released. Other options could be a knot or other mechanical hindrance, when the slot provided for the strings is larger in the releasing position. The slider could also comprise a blade that cuts the strings loose from the plunger.

It is obvious to a person skilled in the art that, in accordance with the above description, the locking means can be of any other kind than those specifically listed above as well as a combination of any of the embodiments and features described above.

The inserter according to the present invention may thus also comprise locking means for reversibly locking the intrauterine system in relation to the plunger, said locking means being controllable by the slider and/or the insertion tube or the plunger itself. This means that the locking means can be controlled also by a part of the slider and/or of the insertion tube, and /or of the handle, such as an extension of one, two or all of them. The handle may also comprise means to control the locking means. The reversible locking of the intrauterine system can be achieved by locking the removal string or strings of the intrauterine system, in such a way that the device remains immobile in relation to the plunger during the necessary steps prior to and during insertion but is automatically released as soon as the IUS has correctly been positioned in the uterus, i.e. at the position when the second end of the slider and the second end of the opening in the handle abut. Therefore no manual handling of the strings as such is needed, which increases security and hygiene and eliminates the possibility of user-made mistakes.

According to another embodiment of the invention, the inserter further comprises a flange arranged on the insertion tube. This flange can be adjusted to correspond to the depth of the uterus in order to correctly position the device during its insertion.

The invention further relates to a kit comprising an intrauterine system and an inserter according to the present invention. The intrauterine system can be any device known in the art as long as these can be managed to enter the insertion tube by appropriate arrangements. Any details and embodiments listed above naturally apply mutatis mutandis to the kit according to the invention.

The present invention also relates to a method for positioning a intrauterine system in a uterus of a patient, wherein the method uses an inserter according to the present invention. The method comprises the steps of moving the slider towards the first end of the opening until the first end of the opening is in contact with the first end of the slider, at this point the intrauterine system is substantially inside the insertion tube, introducing the inserter into the uterus of the patient until the intrauterine system is in correct depth and location, moving the slider towards the second end of the opening until the second end of the opening is in contact with the second end of the slider, at this point the intrauterine system is released from the inserter, and withdrawing the inserter from the uterus of the patient.

The method advantageously contains, at its beginning, the further steps of sounding the uterus using a probe, and setting the flange accordingly to show the correct insertion depth.

An example of the method for positioning the intrauterine system is given hereafter. To insert the IUS only few steps are needed. When the sterile package is opened, the IUS is in a correct configuration relative to the inserter and there is no need to align the frame of the device. The IUS is positioned at the forward end of the plunger with the lower end of the IUS abutting the tip of the plunger and being preferably partly inside the insertion tube, while major part of the IUS remains outside the insertion tube the frame in its expanded configuration in order to prevent fatigue. The removal string(s) attached to the IUS, running in the groove of the plunger and ending at the end of the plunger, are immobilised by the locking means to keep the IUS at a steady and correct position until it is finally released in the uterus.

Then, the handle is hold tightly and the slider is pushed towards the IUS until the first pair of stop members gets together, thereby stopping the movement of the insertion tube and the plunger. At this moment the IUS is substantially inside the insertion tube at a correct depth, and ready for insertion. The distance the insertion tube and the plunger apart from each other from the preliminary position substantially corresponds to the compressed length of that part of the IUS lying originally outside the insertion tube.

The inserter is introduced into the uterus until the IUS is in the correct location, which is determined beforehand by using a probe. Then the slider is retracted towards the second end of the handle all the way until the second pair of stop members gets together. At this moment the removal strings are unlocked and the IUS is released in the uterus. Finally the inserter is withdrawn.

As mentioned, prior art intrauterine devices and delivery systems are usually assembled together with an inserter so that the device is in the expanded form and completely outside the inserter to prevent fatigue of the frame material. To prepare for the insertion the IUD needs first to be pulled inside the insertion tube, and this has to be done in a correct angle and position as regards to the tip of the inserter, otherwise the edges of the insertion tube will damage the loop, possibly also the drug cylinder or the frame may be twisted. This on turn may cause the device to be stuck in the inserter. If the loop will not turn to a correct position and pulling is still continued, the removal string will be cut through the loop, and the device cannot be used any more.

The inserter according to this invention comprises a locking means for reversibly locking the intrauterine system in relation to the plunger via removal string(s) of the intrauterine system, said locking means being attached to the movable plunger. In the original, starting position the lower part of the frame and/or of the therapeutic component is at least partly arranged inside the first end of the insertion tube and IUS is thus parallel to the axis of the plunger and the insertion tube. The removal strings are locked to keep the IUS immobilized with respect to the plunger. The insertion process and management of the removal strings are solely performed by moving the slider. These facts will all together ensure that the IUS will be retracted in the insertion tube in a correct angle and in a direction parallel to the longitudinal axis of the plunger and the insertion tube, thus resulting in a safe and accurate method to retract the IUS in the inserter, as well as to position the IUS and release it in a correct way in the uterus.

The use of the slider mechanism with two distinct operational positions leads to an accurate and straightforward method to control the movement and release of the IUS and the insertion procedure as a whole. The slider-driven operation together with the locking means obviates the manual handling of the removal string(s), thus reducing the risk of damaging the device as well as the risk of contamination or damage by the hands of the operator. Further, since the slider is capable of generating the movement of the insertion tube and the plunger at the same time but to opposite directions, the relative movement of the insertion tube during the insertion steps will be shorter as compared to previous inserters, which increases the accuracy of the insertion and minimizes the possibility of the IUS to be stuck in the insertion tube.

DETAILED DESCRIPTION OF THE DRAWING

In the following description, the term slider and the corresponding reference number are used to designate both the slider mechanism itself and the means to move the slider attached to the slider. The term slider is thus used for convenience of reading.

Figure 1:
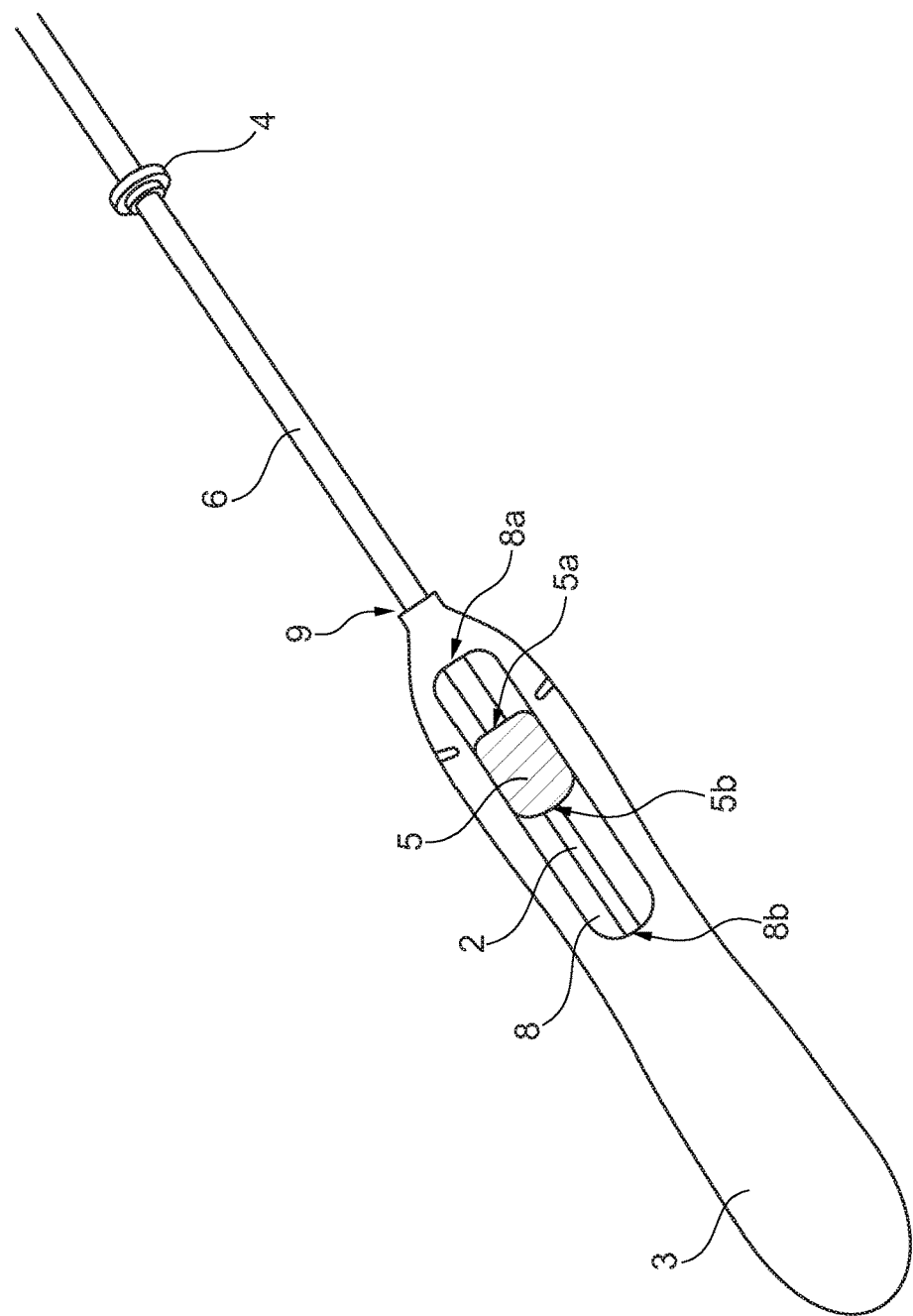
FIG. 1 illustrates a general overview of an inserter according to the invention.

FIG. 1 illustrates a general overview of an inserter according to the invention. The inserter comprises a handle 3, a plunger 2, a slider 5, and an insertion tube 6 around the plunger, the second end of the insertion tube being attached to the slider or to the means to move the slider. The inserter also comprises means for reversibly locking the string(s) (not shown) in such a way that the IUS remains immobile in relation to the plunger during the necessary steps prior to and during insertion, and again for releasing the string(s) and the IUS after it has been inserted. The inserter further comprises an opening 8 in a part of the handle, a channel 9 in which the insertion tube and the plunger slide in the longitudinal direction, and a flange 4, which can be adjusted so that its distance from the first end of the insertion tube corresponds to the depth of the uterus.

The handle 3 has an opening 8 having a first end 8a and a second end 8b, which opening runs in the direction of the plunger 2. The surface of the first end 5a of the slider 5 and the surface at the first end 8a of the opening 8 together form a first pair of stop members, and the surface of the second end 5b of the slider 5 and the surface at the second end 8b of the opening 8 together form a second pair of stop members. When inserting the IUS, the slider can be moved forward until the surfaces 8a and 5a contact each other, and backwards until the surfaces 5b and 8b contact each other. The locking means is arranged on the plunger inside the handle 3 and is thus not visible.

Figure 2A:
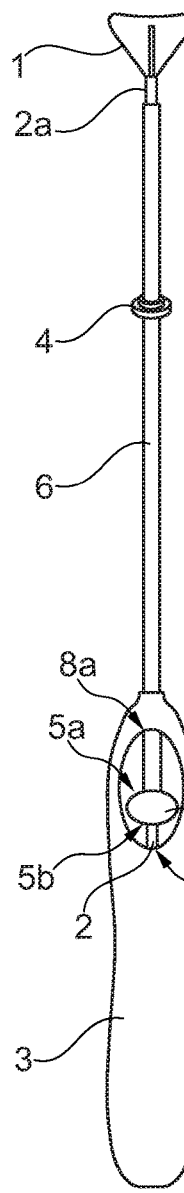
FIGS. 2A, 2B and 2C illustrate an operating principle of an inserter according to an embodiment of the invention.
Figure 2B:
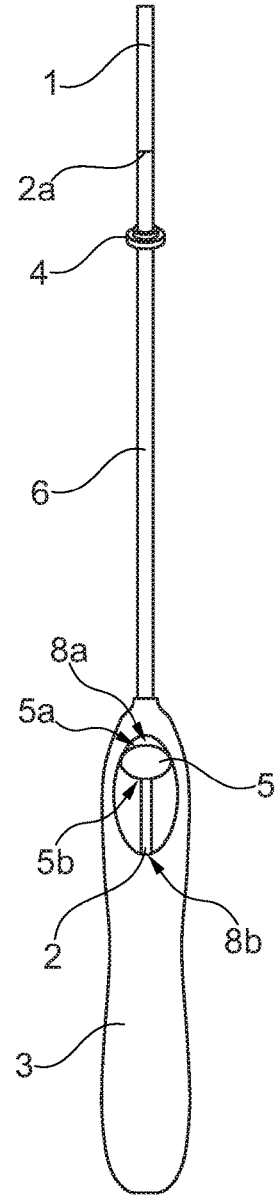
Figure 2C:
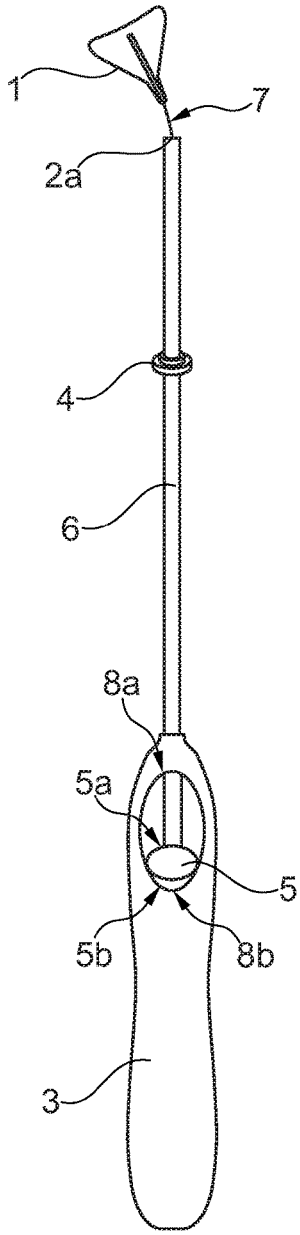
Figure 3A:
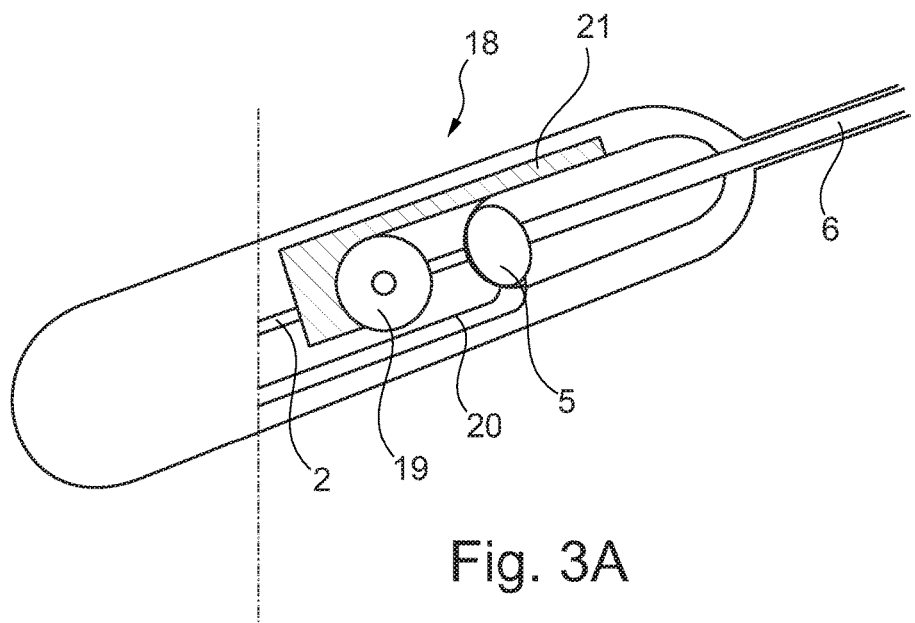
FIGS. 3A, 3B, 3C, and 3D illustrate embodiments of the movement means according to the present invention.
Figure 3B:
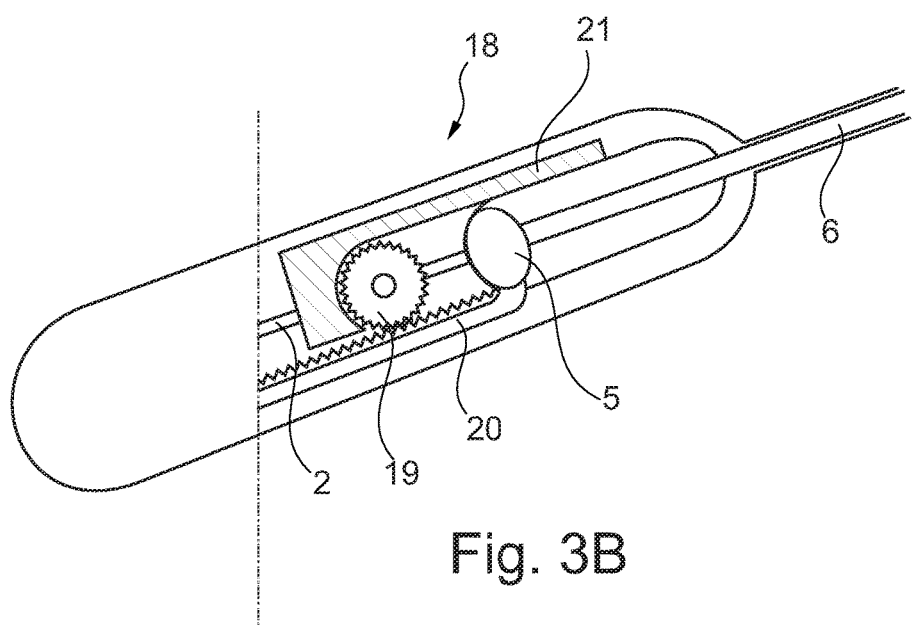
Figure 3C:
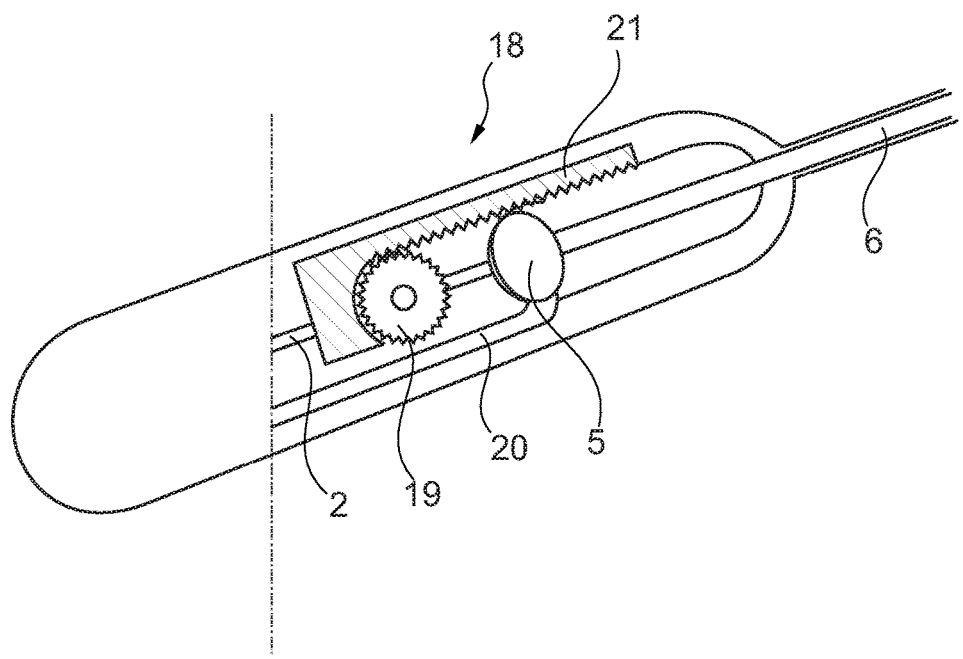
Figure 3D:
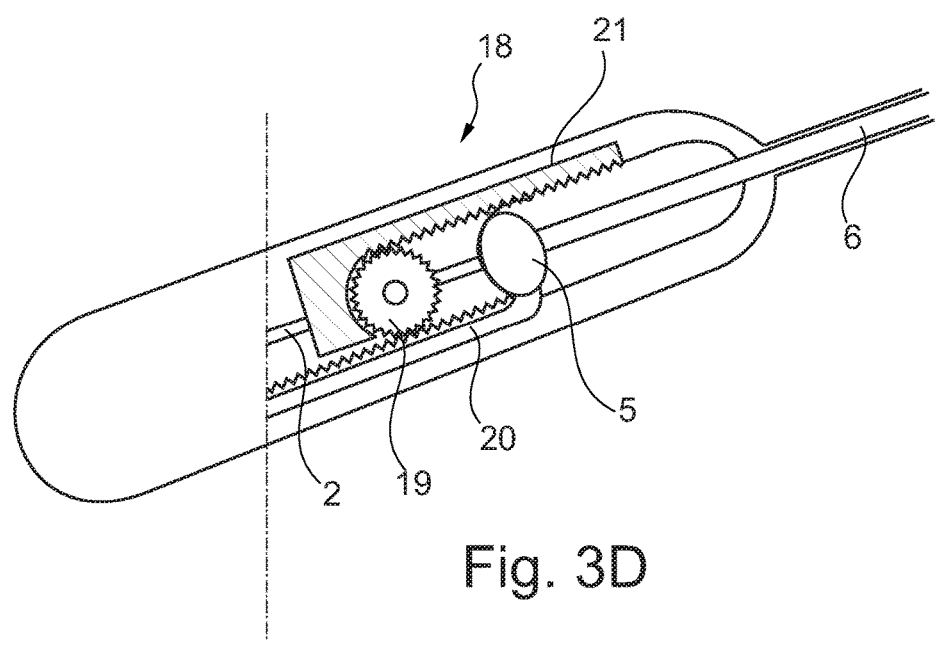

FIGS. 2A, 2B and 2C illustrate an operating principle of an inserter according to an embodiment of the invention FIG. 2A illustrates an inserter and an IUS 1 having a triangular frame in a configuration as they are in a sterilized package. The IUS is placed in the first end (i.e. the front end, i.e. the end of entry into the uterus) of the inserter so that the lower part of the device is partly inside the insertion tube 6 with the bottom tip of the device abutting the end of the plunger (shown with reference number 2a). The means to move the slider 5 is on the starting or initial position, and the removal string(s) inside the inserter are tightened and locked by the locking means (not shown in the Figure).

FIG. 2B illustrates the first step of insertion procedure, wherein the IUS is retracted inside the insertion tube. While holding the handle 3, the slider is moved towards the IUS until surface 5a abuts the surface 8a of the opening 8 of the handle 3, thereby stopping the movement of the slider. When the slider is moved the insertion tube moves forward and at the same time the plunger moves backwards. The distance the plunger and the insertion tube will move relative to each other has been designed substantially to correspond to the length of the IUS assembled for insertion (as explained above).

FIG. 2C illustrates the procedure to release the IUS. The inserter in the configuration according to FIG. 2B is introduced into the uterus until the IUS is in the correct location. The IUS is released from the insertion tube by retaining the inserter stationary and retracting the slider backwards until the surface 5b of the slider abuts the surface 8b of the opening 8 of the handle 3. When the slider is moved the insertion tube will move backwards and simultaneously the plunger will move forward. At a certain point, i.e. when the second stop members 5b and 8b abut, the IUS is substantially outside the insertion tube and at least a part or an extension of the slider and/or the insertion tube or the handle contacts the locking means thus releasing the string(s). The total distance the plunger and the insertion tube can be moved has been selected to indicate clearly the moment at which the IUS has completely been released from the insertion tube and thus corresponds to the length of the IUS being inserted at its compressed state.

FIG. 3 illustrates one embodiment of the movement means according to the present invention. In this Figure, the movement means (18) is shown as comprising a rotation part (19) arranged to rotate around a rotation axis that is perpendicular to the longitudinal axis of the inserter (here the axis perpendicular to the surface of the paper) and a longitudinal movement part (21). Further, the movement means (18) is arranged to move the plunger (2) and the insertion tube (6) simultaneously along the longitudinal axis of the inserter, in opposite directions and is thus in functional connection with the plunger (2) and with the slider (5). Moreover, the slider (5) comprises a longitudinal part (20) that is essentially parallel to the longitudinal part (21) of the movement part and both these parts (20) and (21) are arranged in a functional connection with the rotation part (19).

Figure 4A:
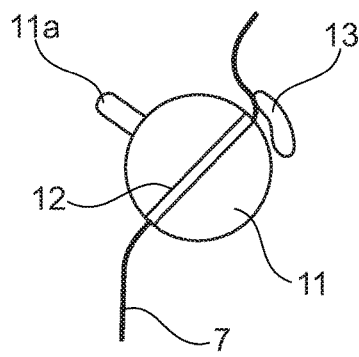
FIGS. 4A and 4B illustrate a locking means according to an embodiment of the invention.
Figure 4B:
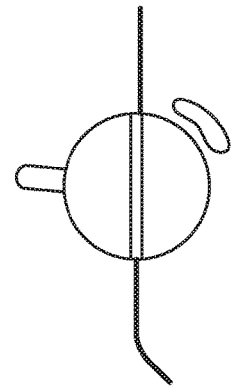

FIGS. 4A and 4B illustrate a locking means according to an embodiment of the invention. The locking means are arranged preferably inside of the handle 3, on the surface of the plunger. The locking means are used to immobilise and release the string(s) of the IUS FIG. 4A illustrates a locking means according to an embodiment of the invention comprising a main part 11 having essentially the shape of a cylinder and comprising an opening 12 there through in a diagonal direction. The string(s) 7 of the IUS pass through the opening 12. The main part 11 is rotatably mounted on the plunger, on a shaft or on an axle (not shown). The locking means also comprises a counterpart 13, such that in the locking position the string(s) are immobilized between the counterpart and the main part. The counterpart thus has a suitable shape adapted to fit to a part of the surface of the main part. When the slider is moving backwards, at a suitable point a part or an extension of the slider, of the insertion tube or of the handle is pressed against the extension 11a of the main part 11 thus turning it enough to release the string(s), as shown in FIG. 4B.

Figure 5A:
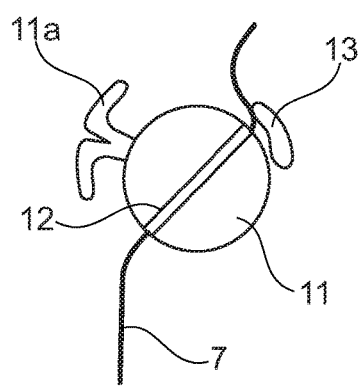
FIGS. 5A and 5B illustrate a locking means according to another embodiment of the invention.
Figure 5B:
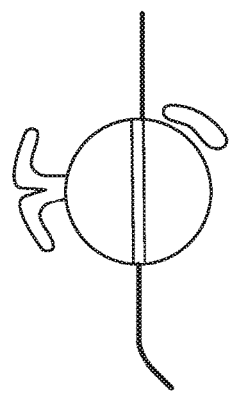

FIGS. 5A and 5B illustrate a locking means according to another embodiment of the invention. FIG. 5A illustrates an object similar to the one presented in FIG. 4A, but having a different construction of the extension 11a.

Figure 6A:
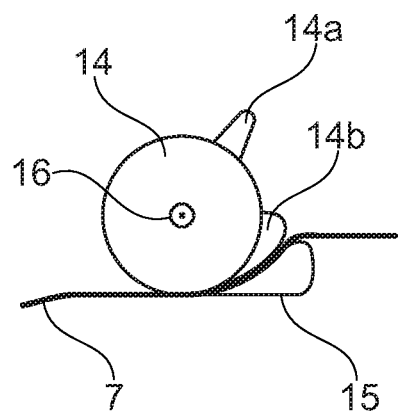
FIGS. 6A and 6B illustrate a locking means according to yet another embodiment of the invention.
Figure 6B:
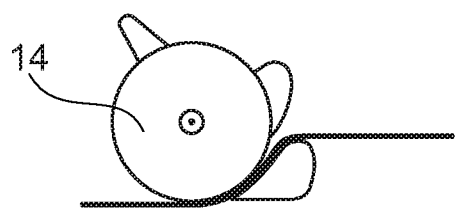

FIGS. 6A and 6B illustrate a locking means according to yet another embodiment of the invention. This is a side view of a locking means having a cylindrically shaped main part 14 which comprises two extensions 14a and 14b. The main part 14 can rotate around a shaft or an axle 16 attached to the plunger. The locking means also comprises a counterpart 15 such that the string(s) 4 are immobilised between the counterpart 15 and the extension 14b. The counterpart 15 has a suitable shape adapted to fit to a part of the surface of the extension 14b. When the slider is moving backwards at a suitable point a part or an extension of the slider, the insertion tube or the handle is pressed against the extension 14a thus turning it enough to release the string(s), as shown in FIG. 6B.

Figure 7A:
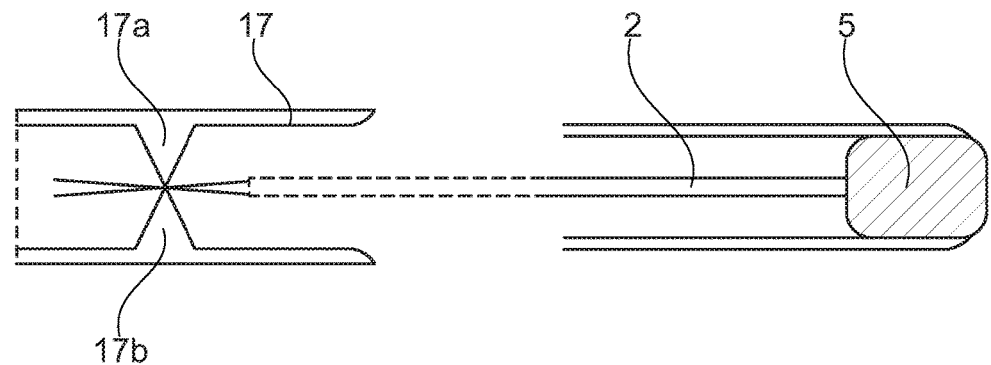
FIGS. 7A and 7B illustrate a locking means according to a further embodiment of the invention.
Figure 7B:
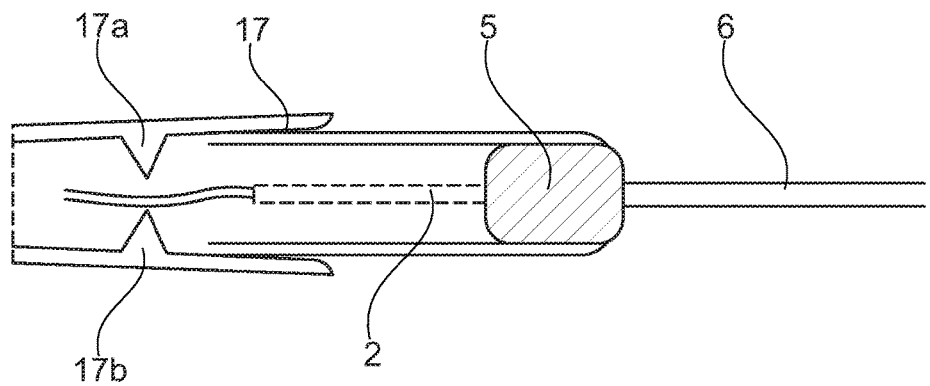

FIGS. 7A and 7B illustrate a locking means according to a further embodiment of the invention. The locking means 17 comprises two extensions 17a and 17b to immobilize the strings as shown in FIG. 7A. When the slider 5 moves backwards at a suitable point a part or an extension of the slider, of the insertion tube or of the handle protrudes into the locking means at least partly to expand the means enough to separate the extensions 17a and 17b and to release the strings, as shown in FIG. 7B.

The invention claimed is:

1. An inserter for an intrauterine system, the intrauterine system including a string, comprising
a handle having a longitudinal opening at its first end, the longitudinal opening having a longitudinal axis parallel to a longitudinal axis of the inserter, a first end, and a second end;
a slider that is arranged in the longitudinal opening, the slider operable to receive a finger of a user, the slider having a first end and a second end, wherein a surface of the first end of the slider and a surface of the first end of the longitudinal opening of the handle form a first pair of stop members as the slider moves upwards along the longitudinal axis of the longitudinal opening and a surface of the second end of the slider and a surface of the second end of the longitudinal opening of the handle form a second pair of stop members as the slider moves downwards along the longitudinal axis of the longitudinal opening, wherein the first pair of stop members indicates when the intrauterine system is retracted in an insertion tube and the second pair of stop members indicates when the intrauterine system is outside the insertion tube and the string of the intrauterine system is released;
a plunger;
the insertion tube arranged around the plunger having a first end and a second end, with the second end attached to the slider and the string of the intrauterine system being positioned inside of the plunger;
a flange arranged on the insertion tube; and
a lock for reversibly locking the intrauterine system in relation to the plunger by immobilizing the string of the intrauterine system between two objects, the lock being attached to the plunger and being controllable by at least one of the slider and the handle, the lock comprising a rotation part arranged to rotate around a rotation axis that is perpendicular to the longitudinal axis of the inserter, the rotation part being arranged in functional connection with the plunger and with the slider, such that movement of the slider generates simultaneous movement of the plunger and of the insertion tube along the longitudinal axis of the inserter, in opposite directions.

2. The inserter according to claim 1, characterized in that:
the slider comprises a longitudinal part,
the lock comprises a longitudinal movement part that is essentially parallel to the longitudinal part, and
the longitudinal part and the longitudinal movement part are arranged in a functional connection with the rotation part.

3. The inserter according to claim 2, characterized in that the longitudinal part and the longitudinal movement part are in the form of a tooth rack, and in that the rotation part is in the form of a cogwheel.

4. The inserter according to claim 1, wherein the two objects of the lock comprise:
a main part forming an opening through which the string passes through, the main part including an extension and
a counterpart, wherein when the lock is in a locked position the string is immobilized between the extension on the main part and the counterpart.

5. The inserter according to claim 1, wherein the two objects of the lock comprise:
a main part forming an opening through which the string passes through and
a counterpart, wherein when the lock is in a locked position the string is immobilized between the main part and the counterpart.

6. The inserter according to claim 1, wherein the two objects of the lock comprise:
two extensions, wherein when the lock is in a locked position the string are immobilized between the two extensions.

7. The inserter according to claim 1, wherein the plunger is hollow, the string slides freely within the plunger, and the first end of the plunger is adapted to receive a lower end of the intrauterine system.

8. The inserter according to claim 1, wherein the intrauterine system is a T-shaped device.

9. A method for positioning of an intrauterine system in a woman's uterus comprising the steps of:
providing the inserter according to claim 1;
moving the slider to abut the first end of the slider and the first end of the longitudinal opening of the handle;
introducing the inserter into the woman's uterus; and
retracting the slider to abut the second end of the slider and the second end of the longitudinal opening.

10. The method according to claim 9, further comprising removing the intrauterine system from the woman's uterus by grasping the string and pulling out the intrauterine system.

* * * * *